United States Patent [19]

Bornengo et al.

[11] 3,997,630
[45] Dec. 14, 1976

[54] PROCESS FOR PREPARING METHYL ESTER OF O,O-DIMETHYL-DITHIOPHOSPHORYL ACETIC ACID

[75] Inventors: Mario Bornengo; Saverio Grego, both of Mestre, Italy

[73] Assignee: Montedison Fibre S.p.A., Milan, Italy

[22] Filed: Mar. 20, 1975

[21] Appl. No.: 560,201

[30] Foreign Application Priority Data

Dec. 3, 1974  Italy .................................. 30136/74

[52] U.S. Cl. ............................... 260/979; 260/941
[51] Int. Cl.$^2$ ......................................... C07F 9/165
[58] Field of Search ........................... 260/979, 990

[56] References Cited

UNITED STATES PATENTS

| | | | |
|---|---|---|---|
| 2,358,133 | 9/1944 | Stoesser et al. | 260/990 X |
| 3,047,459 | 7/1962 | Perini et al. | 260/979 X |
| 3,591,666 | 7/1971 | Pellegrini et al. | 260/990 |

*Primary Examiner*—Anton H. Sutto

[57] ABSTRACT

The methyl ester of O,O-dimethyl-dithiophosphoryl acetic acid is prepared with minimal formation of by-products by reacting the sodium salt of O,O-dimethyl-dithiophosphoryl acid with the methyl ester of 2-chloroacetic acid at a pH of 5.5 to 7, at relatively high temperatures, of the order of 80° to 100° C, for reaction times of 10 to 15 minutes. The process can be carried out continuously.

3 Claims, No Drawings

PROCESS FOR PREPARING METHYL ESTER OF O,O-DIMETHYL-DITHIOPHOSPHORYL ACETIC ACID

THE PRIOR ART

Italian Pat. No. 561,701, assigned to Montecatini, discloses the preparation of N-monomethylamide of O,O-dimethyl-dithiophosphoryl acetic acid from the sodium salt of O,O-dimethyl-dithiophosphoric acid and 2-chloroacetyl-N-acetamide, according to the following reaction:

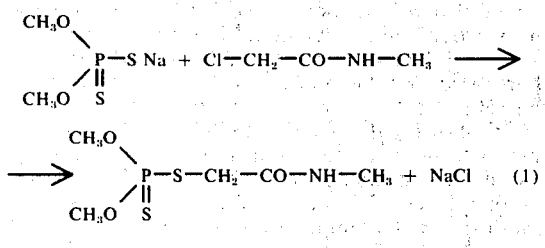

A successive Italian Pat. No. 599,091, (also assigned to Montecatini), noting that the yields obtained by reaction (1) are relatively poor and that said reaction is accompanied by the formation of considerable quantities of by-products, among which the most difficult to remove is the O,O-S-trimethylester of dithiophosphoric acid having the formula

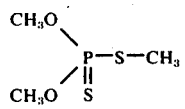

described a two-step process for increasing the yield and reducing the amount of by-products formed during reaction (1).

In the first step of said two-step process, the sodium salt of O,O-dimethyl-dithiophosphoric acid is reacted with the methyl ester of 2-chloroacetic acid, with the formation of the methyl ester of O,O-dimethyl-dithiophosphoryl acetic acid; in the second step said methyl ester is reacted with monomethylamine to obtain the desired amide.

The reactions are as follows:

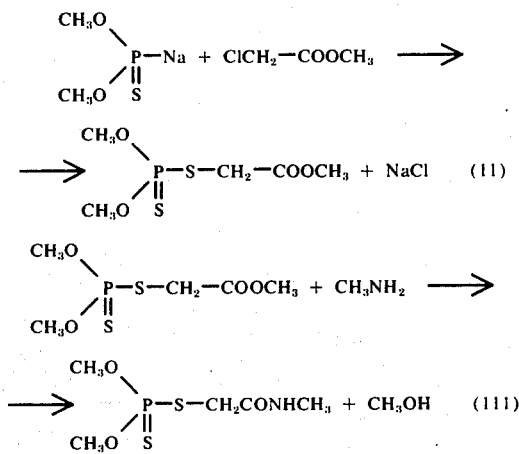

Reaction (11) must be carried out at a relatively high temperature in order to attain a satisfactory reaction speed. On the other hand, the rate of decomposition of the product is proportional to the temperature. According to the indications in Italian Pat. No. 599,091, the reaction occurs at temperatures comprised between 50° C and 55° C under stirring for 6 hours. If the operation is conducted at higher temperatures, the reaction time may be reduced but there is a considerable increase in the impurities. At lower temperatures, longer reaction times are required and in this case, too, high-boiling impurities are formed, mainly the trimethylester of O,O-dithiophosphoric acid which is difficult to remove.

Many impurities are also formed during distillation under vacuum of the methyl ester of O,O-dimethyl-dithiophosphoryl acetic acid due to thermal degradation thereof. These are high-boiling impurities part of which remain in the boiler and part of which are dragged along by the ester and are difficult to remove at a later stage.

THE PRESENT INVENTION

An object of this invention is to provide a process for the preparation of the methyl ester of O,O-dimethyl-dithiophosphoryl acetic acid in which the formation of by-products is minimized.

We have found that this and other objects are achieved by reacting the sodium salt of O,O-dimethyl-dithiophosphoric acid with the methyl ester of 2-chloroacetic acid at a pH of 5.5 to 7, at relatively high temperatures, of the order of 80° C to 100° C, for reaction times of 10 to 15 minutes.

Under these correlated conditions, there is a complete reaction with little formation of by-products. Thus, if the methyl ester of O,O-dimethyl-dithiophosphorylacetic acid produced is stripped in counter-current with steam at 60° C to 65° C, under an inside pressure of 140–150 mm Hg, and with a volumetric steam/ester ratio of about 10 to 25:1, only small quantities of low-boiling by-products are formed which can be readily and rapidly removed.

Preferably, the reaction is conducted by preheating the reactants as fast as possible before the reaction starts, and then starting the reaction.

According to one embodiment of the present invention, preheating of the reactants, initiation of the reaction, and completion of the reaction occur in a cascade with a dwelling time of about 5 minutes in each vessel, under vigorous stirring and, if needed, in the presence of a neutralizing agent such as, for instance, sodium bicarbonate, for attaining the desired pH.

At the outlet of the condensation reactor or reactors, the methyl ester of O,O-dimethyl-dithiophosphoryl acetic acid is generally washed with water and then passed on to the stripping in a thin layer and in counter-current with steam in the aforesaid steam/ester ratio. The low-boiling oils are gathered and separated in the head of the column, while the purified ester, which is gathered at the bottom, goes to amidation, preferably after washing thereof with water. The product thus obtained has a very high titer, the content of undesired and noxious trimethyl ester being, at most, 0.2%. As is known, O,O-dimethyl-dithiophosphoryl acetic acid is a valuable intermediate for the production of pesticides, such as the amide referred to herein.

The following example is given to illustrate the invention in more detail.

EXAMPLE

Into three reactors provided with stirrer, dipping thermometer and reflux condenser, connected in cascade by overflowing, were fed in continuously and contemporaneously:

| | |
|---|---|
| a 38% aqueous solution of the sodium salt of O,O-dimethyldithiophosphoric acid; | 1.696 g/hr |
| methyl 2-chloroacetate at 94%; and | 461.6 g/hr |
| a 10% $Na_2CO_3$ solution | 107.4 g/hr |

In each reactor the dwelling time was 5 minutes under vigorous stirring. In the first reactor the inside temperature was maintained around 80° C and it acted as pre-heater, while in the second and third reactors the temperature was maintained at 98° C.

The liquid flowing out of the reactors was cooled in a condenser and then gathered in a decanter wherein the raw ester separated on the bottom and was then washed and conveyed to a pre-heater which at 80° C brought it to the head of a stripping column (diameter = 30 mm. height = 1500 mm; filled with Rashing rings and thermostabilized at 90° C) in counter-current with steam under the following conditions:

| | |
|---|---|
| feed of the raw ester | 150 g/l of column/hr |
| feed of steam | 205 g/l of column/hr |
| temperature in the column head (outlet) | 60° C |
| residual pressure | 160 mm Hg |

The steam formed an azeotrope with the impurities present with a. b.p. of 60°–65° C, under a pressure of 140–160 mm Hg, gathered in the column head.

The ester came down to the bottom of the column where, after a washing, it was ready for the successive phase. The titer of the pure product was 98%, while the yield amounted to 78% (calculated on the loaded methyl chloroacetate).

We claim:

1. An improved continuous process for the preparation of the methyl ester of O,O-dimethyl-dithiophosphorylacetic acid, which comprises mixing an aqueous solution of the sodium salt of O,O-dimethyl-dithiophosphoric acid with the methyl ester of 2-chloroacetic acid at a pH of 5.5 to 7.0 at a temperature of from 80° C to 100° C allowing the reaction to proceed, for a reaction time of from 10 to 15 minutes, in absence of organic solvents, and stripping the methyl ester of O,O-dimethyl-dithiophosphorylacetic acid thus produced in a current of steam at a temperature of 60° C to 65° C, under a pressure of 140 to 150 mm Hg, and at a volumetric steam to ester ratio of 10:1 to 20:1.

2. The process of claim 1, in which the sodium salt of O,O-dimethyl-dithiophosphoric acid and the methyl ester of 2-chloroacetic acid are both pre-heated as rapidly as possible to a temperature of 70° C to 80° C before the reaction between them is initiated.

3. The process of claim 1, in which the methyl ester of O,O-dimethyl-dithiophosphorylacetic acid is washed with water before it is stripped in the steam current.

* * * * *

UNITED STATES PATENT OFFICE
CERTIFICATE OF CORRECTION

Patent No. 3,997,630      Dated December 14, 1976

Inventor(s) Mario BORNENGO et al

It is certified that error appears in the above-identified patent and that said Letters Patent are hereby corrected as shown below:

Heading, item [73] should read

– – – Montedison S.p.A., Milan, Italy – – –;

not "Montedison Fibre S.p.A., Milan, Italy".

Signed and Sealed this twelfth Day of July 1977

[SEAL]

Attest:

RUTH C. MASON  
*Attesting Officer*

C. MARSHALL DANN  
*Commissioner of Patents and Trademarks*